United States Patent [19]
Gibson

[11] Patent Number: 6,020,507
[45] Date of Patent: Feb. 1, 2000

[54] SYNTHESIS OF PACLITAXEL FROM BACCATIN III BY PROTECTION OF THE 7-HYDROXYL OF BACCATIN III USING A STRONG BASE AND AN ELECTROPHILE

[75] Inventor: Francis S. Gibson, Dayton, N.J.

[73] Assignee: Bristol-Myers Squibb Company, Princeton, N.J.

[21] Appl. No.: 09/252,956

[22] Filed: Feb. 18, 1999

Related U.S. Application Data

[60] Provisional application No. 60/076,493, Mar. 2, 1998.

[51] Int. Cl.⁷ .................................................. C07D 305/14
[52] U.S. Cl. ........................................... 549/510; 549/511
[58] Field of Search ...................... 549/510, 511

[56] References Cited

U.S. PATENT DOCUMENTS

| | | | |
|---|---|---|---|
| 5,274,124 | 12/1993 | Holton | 549/214 |
| 5,399,726 | 3/1995 | Holton et al | 549/510 |
| 5,739,362 | 4/1998 | Holton et al. | 549/510 |
| 5,770,745 | 6/1998 | Swindell et al. | 549/510 |

OTHER PUBLICATIONS

Kingston, D.G.I. et al, "Synthesis of Taxol from Baccatin III via an Oxazoline Intermediate", Tetrahedron Letters, vol. 35, No. 26, pp. 4483–4484, 1994.

Denis, J.N. et al, "A Highly Efficient, Practical Approach to Natural Taxol", J. Am. Chem. Soc., 1988, 110, 5917–5919.

Houlihan F. et al, "Phae transfer catalysis in the tert–butyloxycarbonylation of alcohols, phenols, enols, and thiols with di–tert–butyl dicarbonate", Can. J. Chem. vol. 63, pp. 153–162, 1985.

Nicolaou, K.C. et al, "Chemistry and Biology of Taxol" Angew. Chem. Int. Ed. Engl., 1994, 33, pp. 15–44.

Dasgupta et al, J. Med. Chem., vol. 37, No. 18, pp. 2976–2980, 1994.

*Primary Examiner*—Ba K. Trinh
*Attorney, Agent, or Firm*—Barry J. Marenberg

[57] ABSTRACT

Process for synthesizing paclitaxel by treating baccatin III with a strong base in a solvent, adding an electrophile to the solution to form a 7-O-protected baccatin III derivative, reacting the 7-O-protected baccatin III derivative with a protected paclitaxel sidechain in a solvent such that the protected paclitaxel sidechain is coupled to the 13-hydroxyl of the 7-O-protected baccatin III, and subsequently deprotecting the protected paclitaxel sidechain and the 7-O protecting group to form paclitaxel, and intermediates used therein.

18 Claims, No Drawings

SYNTHESIS OF PACLITAXEL FROM BACCATIN III BY PROTECTION OF THE 7-HYDROXYL OF BACCATIN III USING A STRONG BASE AND AN ELECTROPHILE

This application claims priority benefit under Title 35 §119(e) of U.S. Provisional Application No. 60/076,493, filed Mar. 2, 1998, and entitled SYNTHESIS OF PACLITAXEL FROM BACCATIN III BY PROTECTION OF THE 7-HYDROXYL OF BACCATIN III USING A STRONG BASE AND AN ELECTROPHILE, the entire contects of which are incorporated herein by reference.

BRIEF DESCRIPTION OF THE INVENTION

The present invention is directed to the treatment of baccatin III with a strong base at a low temperature followed by the addition of one or more electrophiles to provide 7-O-protected baccatin III, which can then be converted into Taxol® (paclitaxel). Accordingly, the usefulness of baccatin III as a starting material for Taxol synthesis is demonstrated.

BACKGROUND OF THE INVENTION

Paclitaxel (Taxol), a diterpene taxane compound, is a natural product extracted from the bark of the Pacific yew tree, *Taxus Brevifolia*. It has been shown to have excellent antitumor activity in in vivo animal models, and recent studies have elucidated its unique mode of action, which involves abnormal polymerization of tubulin and disruption of mitosis during the cell cycle. Taxol has recently been approved for the treatment of refractory advanced ovarian cancer, breast cancer and most recently, AIDS-related Kaposi's Sarcoma. The results of paclitaxel clinical studies are replete in scientific periodicals and have been reviewed by numerous authors, such as Rowinsky and Donehower in The Clinical Pharmacology and Use of Antimicrotubule Agents in Cancer Chemotherapeutics, *Phamac. Ther.*, 52, pp. 35–84 (1991); Spencer and Faulds, Paclitaxel, A Review of its Pharmacodynamic and Pharmacokinetic Properties and Therapeutic Potential in the Treatment of Cancer, *Drugs*, 48 (5), pp. 794–847 (1994); K C. Nicolau et al., Chemistry and Biology of Taxol, *Angew. Chem., Int. Ed. Eng.*, 33, pp. 15–44 (1994); F. A. Holmes, A. P. Kudelka, J. J. Kavanaugh, M. H. Huber, J. A. Ajani, and V. Valero, "Taxane Anticancer Agents—Basic Science and Current Status", edited by Gunda I Georg, Thomas C. Chen, Iwao Ojima, and Dolotrai M. Vyas, pp. 31–57 American Chemical Society, Wash., D.C. (1995); Susan G. Arbuck and Barbara Blaylock, "Taxol® Science and Applications", edited by Matthew Suffness, pp. 379–416, CRC Press, Boca Raton, Fla. (1995) and the references cited therein.

A semi-synthetic analog of paclitaxel named Taxotere® (docetaxel) has also been found to have good antitumor activity. The structures of Taxol and Taxotere are shown below along with the conventional numbering system for molecules belonging to the Taxane class; such numbering system is also employed in this application.

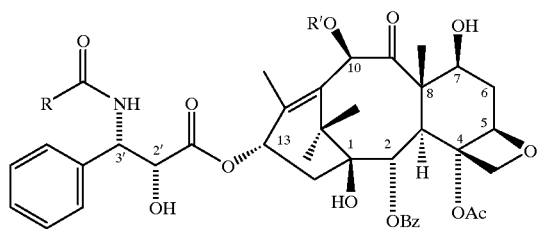

Taxol® (paclitaxel): R=Phenyl; R'=acetyl, 2

Taxotere®: R=t-butoxy; R'=hydrogen

With reference to the numbering of the taxane, reference to a particular carbon on the taxane structure shall be indicated throughout this application by a "C-number", which signifies the carbon on the taxane according to the above numbering system. For example, "C-13" refers to the carbon at position 13 on the taxane ring as shown above, having a sidechain coupled thereto. Additionally, numerals in bold type following compound names and structures refer to the compounds illustrated in the prior art paclitaxel syntheses and Schemes 1–3, hereinbelow The central backbone structural unit of paclitaxel is Baccatin III 1, a diterpenoid having the chemical structure:

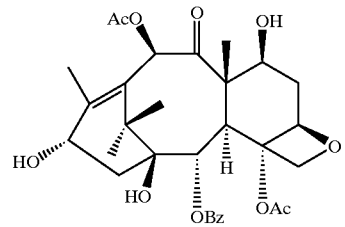

It is also very similar in structure to 10-deacetylbaccatin III 3 ("10-DAB"), which has the chemical structure:

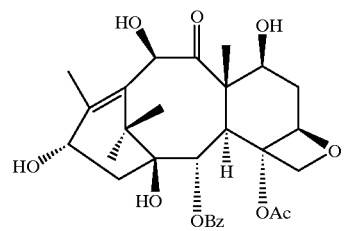

but which lacks an acetate ester at the 10-position alcohol.

Commercial pharmaceutical products containing paclitaxel are available, e.g. for the treatment of ovarian and breast cancer, and most recently, AIDS-related Kaposi's Sarcoma. Paclitaxel has also shown promising results in clinical studies for the treatment of other cancers. As a result, the demand for paclitaxel continues to escalate, and ever increasing amounts of paclitaxel are needed with each passing year for continued research and clinical studies. Paclitaxel is extracted with difficulty and in low yields for the bark of *Taxus brevifolia* (approximately 1 kg. of the drug is isolated from the bark of 3,000 *T. brevifolia* trees). Because of the difficulty in extracting adequate yields, alternative sources for synthesizing paclitaxel are needed.

10-DAB is currently the starting material for the semi-synthesis of paclitaxel, and may be readily extracted from the needles and twigs of the European Yew tree, *Taxus baccata* L. Baccatin III, 10-DAB and other taxane compounds, do not, however, exhibit the degree of antitumor activity demonstrated by paclitaxel. Accordingly, the semi-synthesis of paclitaxel from baccatin III, 10-DAB and other taxane compounds is of great interest and importance.

The structural similarity of 10-DAB to taxol belies, however, the difficulty in converting 10-DAB into taxol, and in fact renders this conversion highly problematical. The required differentiation of the similarly reactive C-7 and C-10 hydroxyl functions and the selective esterification of the difficulty accessible C-13 hydroxyl group with the bulky and suitably protected N-benzoylphenylisoserine (β-amido ester) sidechain of taxol, in practice, can be achieved only with specific protecting groups and under specially developed reaction conditions. J. N. Denis et al., A Highly Efficient, Practical Approach to Natural Taxol, *J. Am. Chem. Soc.* 110, pp. 5917–5918, 1988. This esterification at C-13 is a coupling reaction step which, although tedious due to its location within the concave region of the hemispherical taxane skeleton and because of significant steric hindrance around this position and by hydrogen bonding between the 13-hydroxyl and the 4-acetoxyl group, is a key step required in every contemplated synthesis of taxol or biologically active derivative of taxol, as the presence of the sidechain at C-13 is required for anti-tumor activity. Wani et al., *J. Am. Chem. Soc.* 93, pp. 2325 (1971).

Synthetic methods have been previously disclosed in scientific and patent literature. Three different routes for synthesizing paclitaxel known in the literature are discussed hereinbelow. The first two routes utilize 7-O-TES (triethylsilyl) baccatin III 4, obtained from the selective silylation and acetylation of 10-DAB.

First Route of Paclitaxel Synthesis-Prior Art

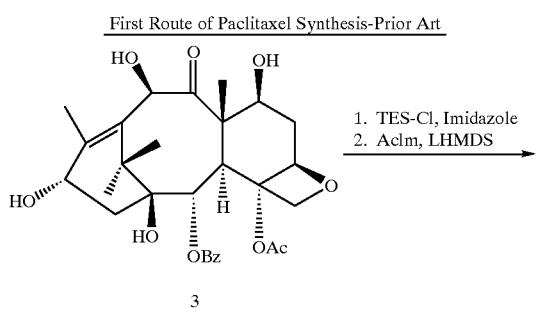

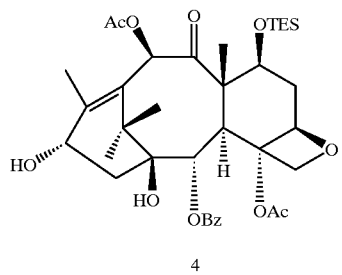

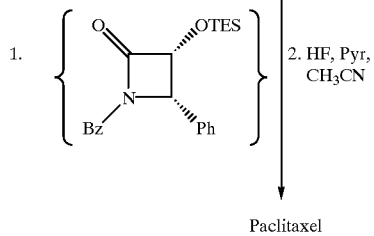

Paclitaxel

The first route, developed by Professor R. A. Holton and disclosed in U.S. Pat. No. 5,274,124, which is incorporated by reference herein, reacts the lithium anion of 7-O-TES-baccatin III 4 with a β-lactam to introduce the required paclitaxel amino acid sidechain at the C-13 position. The 7-O-TES protected baccatin III 4 can be obtained as described by Greene et al in *J. Am. Chem. Soc.* 110, pp. 5917 (1988).

Second Route of Paclitaxel Synthesis-Prior Art

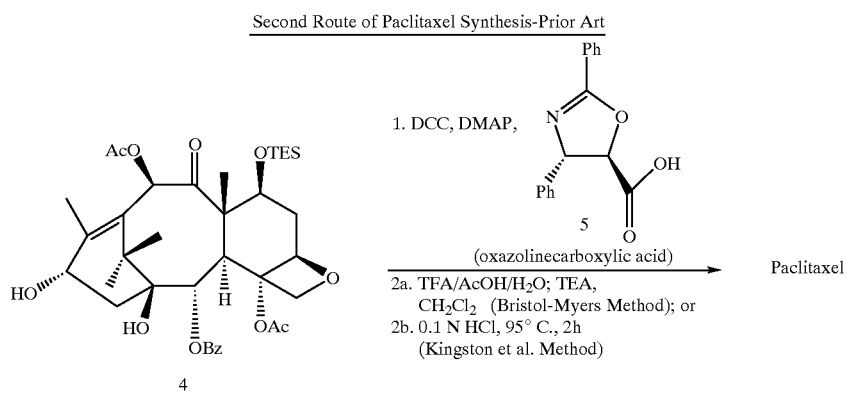

The second route developed by Bristol-Myers Squibb and disclosed in U.S. Pat. No. 5,808,102 and by D. G. I. Kingston et al., in Tetrahedron Letters 35, p. 4483 (1994), both of which are incorporated by reference herein, couples the 7-O-TES-baccatin III 4 with oxazolinecarboxylic acid 5 using DCC or a similar dehydrating agent.

Third Route of Paclitaxel Synthesis-Prior Art

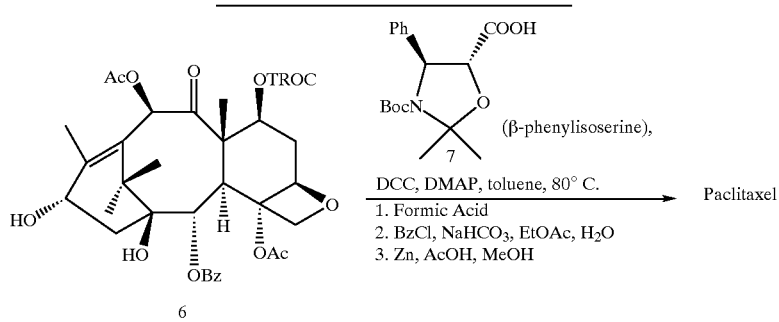

6

A third route of synthesizing paclitaxel from 10-DAB and which couples 7-O-TROC baccatin III 6 with a protected β-phenylisoserine sidechain 7, was developed by A. Commercon et al at Rhone-Poulenc Rorer. A. Commergon et al., Tetrahedron Letters 33, pp. 5185–5188 (1992). This route, however, while producing a significant amount of Taxotere, produces Taxol in much lesser yields.

The use of baccatin III as a starting material would significantly simplify the semisynthesis of paclitaxel. Baccatin III is currently being synthesized by cell culture and could become available in quantities sufficient to support economical and competitive semisynthesis. This would eliminate the need for 10-DAB in the semisynthesis of pacltaxel.

DETAILED DESCRIPTION OF THE INVENTION

It is an object of the present invention to provide a new, useful and efficient protocol for the semi-synthesis of paclitaxel from protected baccatin III derivatives, which comprises the attachment of a paclitaxel sidechain to the protected baccatin III derivatives, followed by subsequent deprotection of the protected baccatin III derivatives.

Another object of the present invention is the provision of methods of producing various baccatin III derivatives having a protecting group at the C-7 site on the taxane structure, and which, after attachment of a sidechain and subsequent deprotection, yields paclitaxel in significant amounts.

An additional object of the present invention is the provision of a simple, efficient, and cost effective protocol for the semi-synthesis of paclitaxel.

Accordingly, the present invention encompasses a novel method by which baccatin III can be efficiently converted to 7-O-protected baccatin III using several different protecting groups. After attachment of a paclitaxel sidechain at the C-13 site, these 7-O-protected baccatin III compounds can then be easily converted into paclitaxel making baccatin III a valuable starting material for the semisynthesis of paclitaxel.

The present disclosure is broadly directed to a chemical process for the efficient production of paclitaxel, intermediates and precursors thereof. More specifically, the present invention is directed to the semi-synthesis of paclitaxel by protecting the 7-hydroxyl of paclitaxel precursor baccatin III to provide 7-O-protected baccatin III, using strong bases, such as lithium tert-butoxide (LitbuO), lithium hexamethyldisilazane (LiHMDS), potassium hexamethyldisilazane (KHMDS) or sodium hexamethyldisilazane (NAHMDS) in DMF or similar known solvents such as DMAC, NMPO, DMEU and DMPU, and various electrophiles followed by the coupling of a paclitaxel sidechain at the C-13 position and subsequent deprotection of the C-7 and replacement of the protecting group with a hydrogen. More particularly, the invention utilizes protecting groups such as benzolyloxycarbonyl (CBZ) or tert-butoxycarbonyl (BOC) at the C-7 site on the taxane during the coupling of the paclitaxel sidechain at the C-13 position.

The general process described herein involves the production of 7-O-protected-baccatin III derivatives, such as 7-O-CBZ- or 7-O-BOC baccatin III, the coupling of a sidechain at C-13, and the subsequent deprotection of C-13 sidechain bearing 7-O-protected-baccatin III intermediate to paclitaxel. A particularly advantageous base for producing 7-O-protected baccatin III is LitbuO, an inexpensive base which provides a good yield and a significantly cleaner product. Other useful electrophiles include those of the general formula

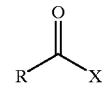

wherein R is alkyl, aryl, R'O—, or R'$_2$N—, RS, and X is halogen, imadozoyl, benztriazole, N-(benzyloxycarboxyloxy) succinimide, OR', or —OOCOR in a solvent such as DMF and wherein R' is alkyl or alkenyl having 1–6 carbons atoms, benzyl, phenyl, trichloroethyl, trifluoroethyl, 2-trimethylislylethyl or triisopropylilyl.

As stated, the 7-hydroxyl of baccatin III is protected with a conventional hydroxy protecting group. Conventional hydroxy protecting groups are moieties which can be employed to block or protect a hydroxy function and they are well known in the art. Preferably, said protecting groups are those which can be removed by methods which result in no appreciable destruction to the remaining molecule. Examples of such readily removable hydroxy protecting groups such as benzyloxycarbonyl, triethylsilyl, 2,2,2-trichloroethoxycarbonyl, and tert-butoxyearbonyl, amongst others. Other suitable protecting groups which may be used are found in Chapter 2 of "Protective Groups in Organic Synthesis", Second Ed., by Theodora W. Greene and Peter G. M. Wuts (1991, John Wiley & Sons, Inc.)

The specific examples which follow illustrate the synthesis of representative compounds of the instant invention and are not to be construed as limiting the invention in sphere or scope. The methods may be adapted to variations in order to produce intermediates and compounds embraced by this invention but not specifically disclosed. Further, variations of the methods to produce the same compounds in somewhat different fashion will also be evident to one skilled in the art.

The abbreviations used herein are conventional abbreviations widely employed in the art. Some of which are:

| | |
|---|---|
| Ac | acetyl |
| AcOH | acetic acid |
| Bz | benzoyl |
| BOC | tert-butoxycarbonyl |
| BOC₂O | di-tert-butylcarbonate |
| CBZ | benzyloxycarbonyl |
| CBZ-Cl | benzyloxycarbonyl chloride |
| DCC | dicyclohexylcarbodiimide |
| DCU | N,N-dicyclohexylurea |
| DMAC | N,N-dimethylacetamide |
| DMAP | 4-dimethylaminopyridine |
| DMEU | N,N'-dimethylethyleneurea |
| DMF | dimethylformamide |
| DMPU | N,N'dimethylpropyleneurea |
| EtOAc | ethyl acetate |
| h | hour(s) |
| ipa | isopropyl alcohol |
| KHMDS | potassium hexamethyldisilazane |
| LiHMDS | lithium hexamethyldisilazine or lithium bis(trimethylsilyl)amide |
| LitbuO | lithium tert-butoxide |
| MeOH | methanol |
| min | minutes |
| MTBE | tert-butylmethyl ether |
| NaHMDS | sodium hexamethyldisilazane |
| NMPO | N-methyl-2-pyrrolidinone |
| Ph | phenyl |
| rt | room temperature |
| tBu | tertiary butyl |
| TES | triethylsilyl |
| THF | tetrahydrofuran |
| TFA | trifluoroacetic acid |
| TROC | 2,2,2-trichloromethoxycarbonyl |

A. Production of 7-O-anion

As a starting point in the semi-synthesis of paclitaxel according the exemplary embodiment of the present invention, baccatin III is reacted with one or more strong bases to provide a 7-O-anion suitable for reaction with an electrophile/protecting reagent. The process of preparing the 7–0 anion is illustrated in Scheme 1.

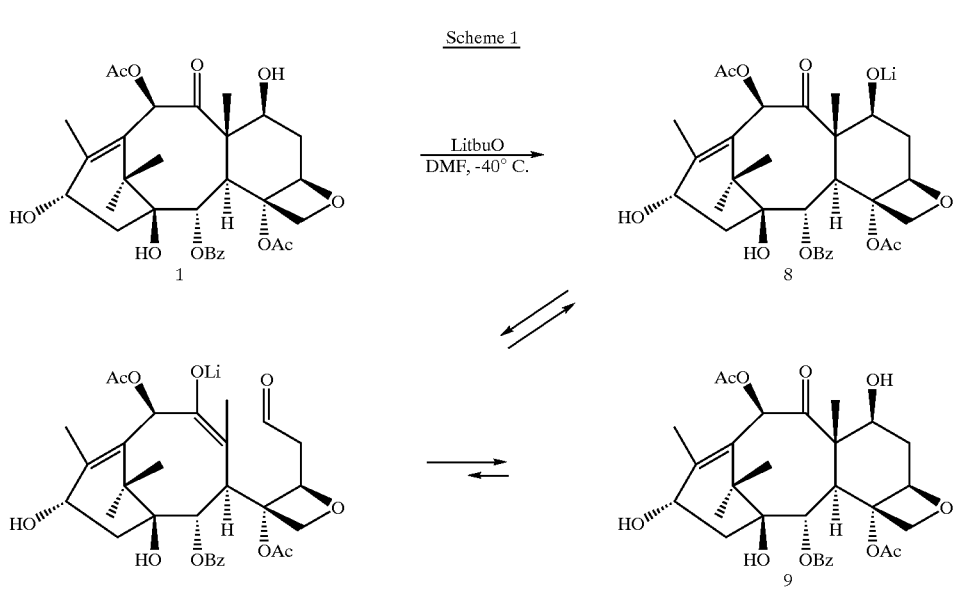

As illustrated in Scheme 1, treatment of a solution of baccatin III 1 in DMF with LitbuO at low temperature produces the 7-O-anion 8. DMF is the preferred solvent, as the reaction is slow in the commonly used THF. Other solvents which may be used include DMAC, NMPO, DMEU and DMPU. The epimer 9 is the favored configuration under these conditions, but surprisingly only the 7-O anion 8 reacts with electrophile. Although LitbuO is the favored base which provides a cleaner product in significant yield, other bases such as LiHMDS, NaHMDS, and KHMDS may also be used.

B. Production of 7-O-Protected-Baccatin III and Synthesis of Paclitaxel Therefrom Using the 7-anion 8 prepared in scheme 1,7-O-protected baccatin III may be prepared and an oxazoline sidechain may be esterified at C-13 according to Scheme 2 and then converted into paclitaxel.

Scheme 2

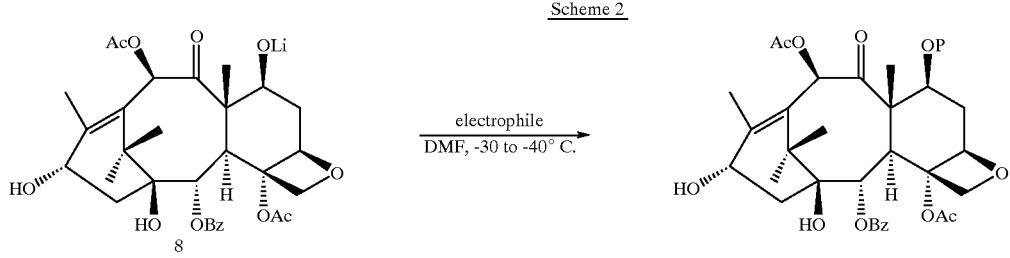

electrophiles = TROC-Cl, CBZ-Cl
CBZ$_2$O, BOC$_2$O, diethylchlorophosphate
isobutyl chlorophormate, acetylimidazole
adamantyl fluoroformate, allyl chloroformate,
vinyl chloroformate 6, P = TROC
10, P = CBZ
11, P = BOC
12, P = diethylphosphate
13, P = ibuOOC
14, P = Ac
15, P = AdOOC
16, P = AllylOOC
17, P = vinylOOC

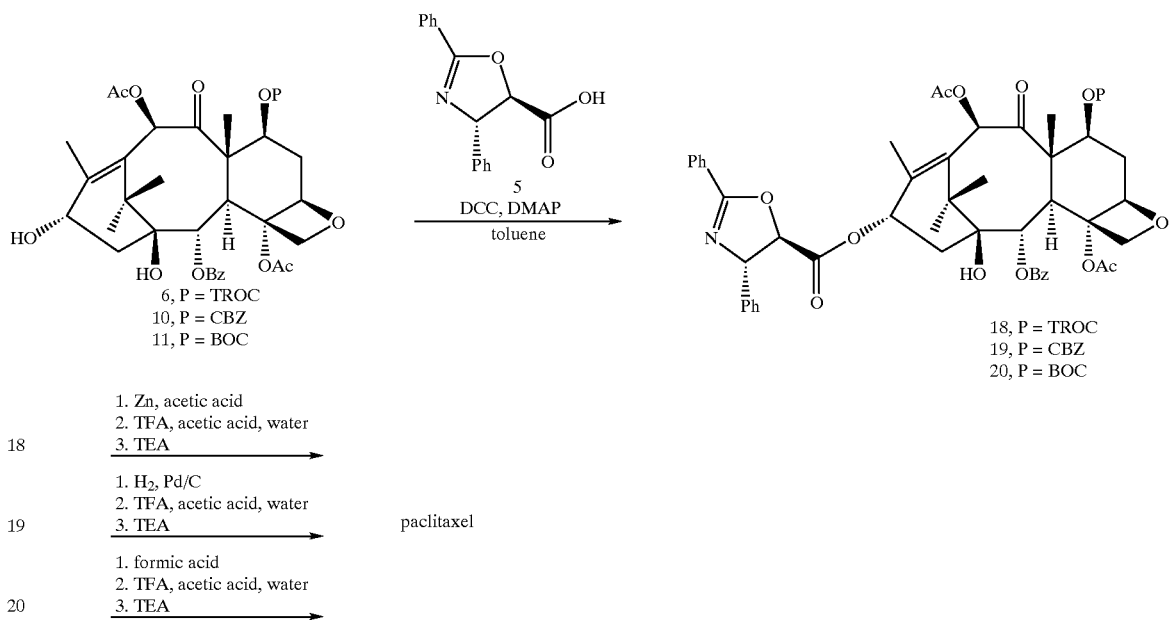

18, P = TROC
19, P = CBZ
20, P = BOC 18    1. Zn, acetic acid
     2. TFA, acetic acid, water
     3. TEA 19    1. H$_2$, Pd/C
     2. TFA, acetic acid, water
     3. TEA     paclitaxel 20    1. formic acid
     2. TFA, acetic acid, water
     3. TEA As illustrated in Scheme 2, addition of a protecting group P, which is advantageously delivered by electrophiles such as, for example, TROC-Cl, CBZ-Cl, CBZ$_2$O, BOC-Cl or BOC$_2$O, results in the formation of the corresponding 7-O-TROC-protected, 7-O-CBZ-protected and 7-O-BOC-protected baccatin III derivatives 6, 10 and 11, respectively. This reaction is rapid and gives little 7,13-bis protected by-product. Other protecting groups, e.g. acyl halides, dialkylphosphates and carbonates, such as diethylchlorophosphate, isobutylchloroformate (ibuOOC), acetate (Ac) adamantyl fluoroformate (AdOOC), allyl chloroformate (AllylOOC), vinyl chloroformate vinylOOC), acetylimidazole and TROC-Cl and also work well in the formation of 7-O-protected baccatin derivatives 12, 13, 14,15, 16 and 17. Simple esters can also be formed, such as acetate, with the use of acetylimidazole. Reaction of the 7-O-protected baccatin derivatives 6, 10, and 11 with oxazoline 5, a protected paclitaxel sidechain, in toluene with DCC and DMAP delivered the corresponding 7-O-protected C-13 sidechain bearing products 18, 19 and 20.

These paclitaxel precursors 18, 19 and 20 may all be converted to paclitaxel 2 by removal of the 7-O-protecting groups by ordinary methods, and by acid hydrolysis of the protected sidechain to β-phenylisoserine.

C. Production of 7-O-Protected Baccatin III and Synthesis of Paclitaxel Therefrom—Alternative Synthesis As illustrated in Scheme 3, 7-O-Protected-Baccatin III derivatives 6, 10, and 11, prepared according the steps illustrated in Scheme 2, may alternatively be coupled with BMOP 24 in LitbuO which is esterified at C-13 and then treated with acid to produce 7-O-protected paclitaxel precursors 21, 22, and 23. These paclitaxel precursors 21, 22, and 23, may then be converted to paclitaxel 2 by removal of the 7-O-protecting groups by ordinary methods, and by acid hydrolysis of the protected sidechain to phenylisoserine.

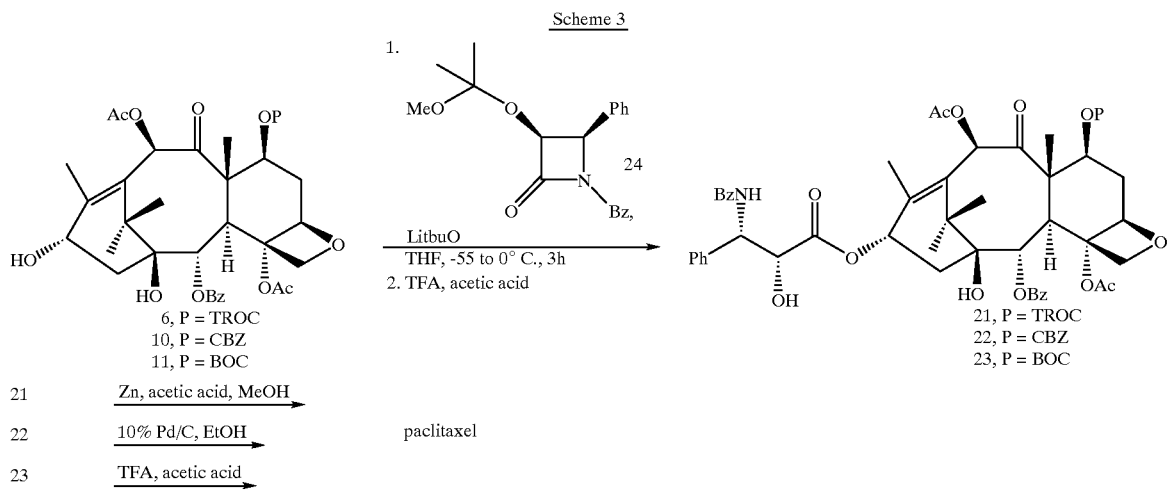

Scheme 3

It is believed that one of ordinary skill in the art can, using the above description perform the processes disclosed and prepare the full scope of the intermediates and compounds of the present invention. The following examples further exemplify the general procedure for the preparation procedures inherent in the synthesis of paclitaxel from Baccatin III.

EXAMPLE 1

Synthesis of 7-O-Acyl-Baccatin III derivatives from Baccatin III

Baccatin III 1 is dissolved in DMF. The resulting solution is cooled to −40 ° C., and LiHMDS (1 M solution in THF) is added. After 5 minutes, the appropriate electrophile is added. The reaction is stirred at −30° C., and extra base or electrophile is added to drive the reaction to completion. The reaction is then quenched with acetic acid and poured in to MTBE. The MTBE solution is washed 3 times with water, the organic layer is concentrated, and the resulting residue is then chromatographed over silica gel (ethylacetate/hexanes) or crystallized to give the title compound a. 7-O-TROC-baccatin III (6)

Using the general procedure, baccatin III (0.150 g, 0.26 mmol) was reacted with LiHMDS (0.52 mL, 2.0 eq) and TROC-Cl (43 μL, 1.2 eq) in 2 mL) of DMF to produce 80 mg (41% of 7-O-TROC baccatin III after silica gel chromatography.

b. 7-O-CBZ-baccatin III (10)

Baccatin III (0.25 g. 0.43 mmol) was dissolved in 4 mL of anhydrous DMF. The solution was cooled to −40° C. and 150 mol % of LiHMDS (1 M in THF, 0.64 mL) was added slowly over 1 min. After 5 min. CBZ$_2$O (150 mol %, 0.185 g) was added as a solution in DMF (0.5 mL), and the reaction was allowed to stir at −35 to −30° C. Extra base was added after 40 min. (0.1 mL), and CBZ$_2$O (40 mg) at one hour. After 3 hours, 1.5 mL of acetic acid was added and the reaction mixture was poured in 25 mL of MTBE. The organic layer was washed with 3×15 mL of water, and then concentrated to an oil. The product was crystallized from MTBE/heptane to give 228 mg of 7-O-CBZ-baccatin III, 82%.

NMR δ 8.0–7.2(m,10 H), 6.35 (s, 1H), 5.54 (d, 1H, J=6.8), 5.47 (dd, 1H, J=7.2, 10.8), 5.12 (dd, 2H, J=12.2, 21.2), 4.88 (d, 1H, J=8.6), 4.76(t, 1H, J=8.1), 4.03 (d, 1H, J=7.2), 3.93 (d, 1H, J=7.2), 2.65–2.40 (m, 1H), 2.30–1.70(m, 5H), 2.20 (s, 3H), 2.10 (s, 3H), 2.00 (s, 3H), 1.70 (s, 3H), 1.10 (s 3H), 0.90 (s, 3H).

c. 7-O-BOC-baccatin III (11)

Using the general procedure, baccatin III (2.076 g, 54 mmol) was reacted with LiHMDS (5.6 mL, 1.5 eq) and BOC$_2$O (1.36 g 1.5 eq) in 24 mL of DMF to produce 1.6 g (75%) of 7-O-BOC-baccatin III after silica gel chromatography.

NMR δ 8.00–7.30 (m, 5H), 6.43 (s, 1H), 5.55 (d, 1H, J=7.2), 5.30 (dd, 1H, J=6.8, 10.4), 4.85 (d, 1H, J=8.6), 4.75 (t, 1H, J=8.1), 4.20 (d, 1H, J=8.6), 4.07 (d, 1H, J=7.3), 3.89 (d, 1H1, J=6.8) 2.60–2.48 (m, 1H), 2,21–2.00 (m, 3H), 2.18 (s, 3H), 2.10 (s, 3H), 2.05 (s, 3H), 1.90–1.78 (m, 1H), 1.68 (s, 3H), 1.60–1.50 (m, 1H), 1.36 (s, 9H), 1.05 (s, 3H), 0.97 (s, 3H).

d. 7-O-diethylphosphoryl-baccatin III (12)

Using the general procedure, baccatin III (0.150 g, 0.26 mmol) was reacted with LiHMDS (0.52 mL, 2 eq.) and chlorodiethylphosphate (45 μL, 1.2 eq) in 2 mL of DMF to produce 110 mg (59%) of 7-O-diethylphosphoryl-baccatin III after silica gel chromatography.

e. 7-O-isobutoxycarbonyl-baccatin III (13)

Using the general procedure, baccatin III (0.150 g, 0.26 mmol) was reacted with LiHMDS (0.52 mL, 2 eq) and isobutylchloroformate (66 μL, 2 eq) in 2 ml of DMF to produce 153 g (87%) of 7-O-isobutoxycarbonyl-baccatin III after silica gel chromatography.

f. 7-O-acetyl-baccatin III (14)

LiHMDS in THF (1 M, 1 mL, 1 mmol) was added over 1 minute to a stirred solution of baccatin III (700 mg, 1.19 mmol) in dry THF and DMF at −45° C. under argon. After 5 min, a solution of acetylimidazole (264.3 mg, 2.4 mmol) in dry DMF (1.5 mL) was added in one minute and stirring was continued for 3 min. The reaction was slowly warmed from −45° C. to −35° C. over 5 min and held for 10 min between −35° C. and −33° C. HPLC indicated the absence of starting material. The reaction was quenched with AcOH (100 μL) and diluted with 15 mL of MTBE, which was then washed with water (5×10 mL) and evaporated to give a while solid (772 mg). This solid was dissolved in 3 mL of toluene at 65° C., to which heptane (12 mL) was added. The resulting slurry was stirred at 65° C. to 29° C. for 45 min and at room temperature for 45 min to give 7-O-acetyl-baccatin III (582 mg) as a crystalline material in 77.6% yield.

g. 7-O-adamantyloxycarbonyl-baccatin III (15)

Using the general procedure, baccatin III (0.150 g, 0.26 mmol) was reacted with LiHMDS (0.52 mL, 2 eq) and adamantyl fluoroformate (101 mg, 2 eq) in 2 mL of DMF to produce 120 mg (64%) of 7-O-adamantyloxycarbonyl-baccatin III after silica gel chromatography.

h. 7-O-allyloxycarbonyl-baccatin III (16)

Using the general procedure, baccatin III (0.200 g, 0.34 mmol) was reacted with LiHMDS (0.68 mL, 2 eq) and allylchloroformate (45 μL, 1.25 eq) in 2 mL of DMF to produce 120 mg g(65%) of 7-O-allyloxycarbonyl-baccatin III after silica gel chromatography.

i. 7-O-vinyloxycarbonyl-baccatin III (17)

Using the general procedure, baccatin III (0.116 g, 0.198 mmol) was reacted with LiHMDS (0.2 mL, 1 eq) and vinyl chloroformate (25 μL, 1.5 eq) in 2 ml DMF to produce 79 mg g (61%) of 7-O-vinyloxycarbonyl-baccatin III after silica gel chromatography.

EXAMPLE 2

General Procedure for Coupling Oxazoline to 7-acyl-baccatin III Derivative Compounds The 7-O-acyl-baccatin III compound is added to dry toluene. DCC, DMAP and oxazoline carboxylic acid 5 are added and the reaction mixture is stirred at rt until HPLC determines that no starting material remains. The reaction is quenched with AcOH, diluted with EtOAc, and filtered to remove DCU. The organic solution is washed with 10% $KH_2PO_4$, 10% $NaHCO_3$, and water, concentrated, and the desired product is isolated by crystallization or silica gel chromatography.

a. 7-O-TROC-13-O-oxazolinoylbaccatin III (18)

Following the general procedure, 7-O-TROC-baccatin III 6 (80 mg, 0.105 mmol) was combined with oxazoline carboxylic acid 5 (34 mg, 0.126 mmol), DMAP (15 mg, 0.126 mmol) and DCC (26 mg )0.126 mmol) in toluene (2 mL) to produce 7-O-TROC-13-O-oxazolinoylbaccatin III (82 mg 77%) after chromatography (hexane/EtOAc 5:2).

b. 7-O-CBZ-13-O-oxazolinoylbaccatin III (19)

Following the general procedure, 7-O-CBZ-baccatin III (262.2 mg, 0.36 mmol) was combined with oxazoline carboxylic acid 5 (117 mg, 0.44 mmol), DMAP (47.2 mg, 0.39 mmol) and DCC (113 mg, 0.55 mmol) in toluene (5 mL) to produce 7-O-CBZ-13-O-oxazolinoylbaccatin III (295 mg, 83.6%) after chromatography (hexane/EtOAc 65:35).

c. 7-O-BOC-13-O-oxazolinoylbaccatin III (20)

Following the general procedure, 7-O-BOC-baccatin III 11 (0.5 g, 0.73 mmol) was combined with oxazoline carboxylic acid 5 (234 mg, 0.88 mmol), DMAP (94.3 mg, 0.77 mmol) and DCC (190.7 mg, 0.93 mmol) in toluene (5.1 mL) to produce 7-O-BOC-13-O-oxazolinoylbaccatin III (641 mg, 94%) after crystallization from isopropyl alcohol.

EXAMPLE 3

Synthesis of Paclitaxel from 7-O-Protected Paclitaxel Precursors a. Paclitaxel from 7-O-CBZ-13-O-oxazolinoylbaccatin III (19)—First Method 7-O-CBZ-13-O-oxazolinoylbaccatin III 19 (100 mg, 0.1 mmol) was dissolved in a solution of TFA (50 μL), AcOH (1.05 mL) and water (0.268 mL). This mixture was stirred at rt for 5 h until no starting material was detected. The solution was quenched with NaOAc (59 mg) in water (0.21 mL) and stirred for 3 min. $CH_2Cl_2$ (10 mL) and water (3 mL) were added and stirring continued for 3 min. The phases were separated and the water layer was extracted with $CH_2Cl_2$ (5 mL). The combined organic layers were washed with water (2×5 mL), concentrated to 1.5 mL and treated with TEA (193 μL). After an hour at rt, the reaction mixture was quenched with concentrated $H_2SO_4$ (0.162 mL) in water (1.444 mL) and extracted with $CH_2Cl_2$ (10 mL). The organic phase was washed with water (2×5 mL), dried over $Na_2SO_4$, and evaporated to give pure 7-O-CBZ-paclitaxel 22 (102.3 mg, 100%). 7-O-CBZ-paclitaxel is then converted to paclitaxel by hydrolysis of this compound (65 mg, 0.08 mmol) was carried out using TFA (38.1 μL, 0,5 mmol), AcOH (0.8 mL), and water (0.203 mL) for 5 h followed by TEA (146.2 μL) for 1 h to provide pure paclitaxel (66.1 mg) in 99.5% yield.

b. Paclitaxel from 7-O-CBZ-13-O-oxazolinoylbaccatin III (19)—Alternate Method

7-O-CBZ-13-O-oxazolinoylbaccatin III 19 (120 mg, 0.12 mmol) in EtOH (20 mL) was hydrogenated with 10% Pd/C (20 mg) and $H_2$ (30 psi) to provide 13-O-oxazolinoyl-baccatin III (99.6 mg), in 96.3% yield. Hydrolysis of this compound (65 mg, 0.08 mmol) was carried out using TFA (38.1 μL, 0,5 mmol), AcOH (0.8 mL), and water (0.203 mL) for 5 h followed by TEA (146.2 μL) for 1 h to provide pure paclitaxel (66.1 mg) in 99.5% yield.

A solution of 7-O-BOC-13-O-oxazolinoylbaccatin III 20 (100 mg, 0.11 mmol) and water (0.3 ml) in AcOH (2.36 ml) was stirred at 75° C. The reaction mixture after 20 h was diluted with methylene chloride (15 ml) and washed with water (3×5 ml). The organic phase was conentrated and purified over a silica gel using hexane-EtOAc (3:7) to furnish paclitaxel (63 mg) in 69.1% yield.

d. Paclitaxel from 7-O-BOC-13-oxazolinoylbaccatin III (20)—Second Method

Trifluoroacetic acid (0.472 ml, 6.13 mmol) was added to a biphasic mixture of 7-O-BOC-13-oxazolinoylbaccatin III (900 mg, 0.96 mmol) in $CH_2Cl_2$ (18 ml) and water (2.7 ml) at room temperature and stirred for 19 h. As no starting material was detected by HPLC, the reaction was quenched with aq NaOAc solution and the phases were separated. The methylene chloride phases contained 2'-OBz-7-BOC-paclitaxel, was treated with TEA (1.8 ml, 12.9 mmol). After 23 h at room temperature, the reaction mixture was quenched with diulted $H_2SO_4$ at 15° C. The organic phase obtained after separation was washed with water (2×10 ml) and evaporated to a foamy solid, which on crystallization from IPA-hexane afforded 7-O-BOC-paclitaxel (782 mg) in 85.2% yield. Cold formic acid (99%, 5 ml, 10° C.) was added to 7-O-BOC-paclitaxel (500 mg, 0.52 mmol) in a flask at 7° C. and the resulting solution was stirred at 7–10° C. for 45 min. The reaction mixture was diluted with methylene chloride (40 ml) and washed with water 4×10 ml). Evaporation of the organic phase gave a foamy solid, which was crystallized from IPA to furnish paclitaxel (284.7 mg) in 63.3% yield.

c. Paclitaxel from 7-O-BOC-13-O-oxazolinoylbaccatin III (20)—Third Method

7-O-BOC-13-O-oxazolinoylbaccatin III 20 (450 mg, 0.54 mmol) was treated with TFA (0.273, 3.54 mmol), AcOH (5.71 ml) and water (1.048 ml) at room temperature for 7 h followed by TEA (1.01 ml, 7.25 mmol) for 0.5 h to give paclitaxel (310 mg) in 64.7% yield after crystallization from IPA.

EXAMPLE 4

General Procedure for Coupling BMOP Sidechain to 7-O-acyl-baccatin compounds A solution of 7-O-acyl-baccatin III in THF at −55° C. is treated with LiHMDS (1M in THF). A solution of BMOP in THF is added and the reaction is stirred at 0° C. for 3h. Water is added to quench the reaction, and the mixture is poured into EtOAc. The organic layer is washed with water and brine, dried over Na$_2$SO$_4$, and concentrated. The resulting product is re-dissolved with AcOH and treated with TFA. The reaction is quenched with aq. NaOAc, diluted with CH$_2$Cl$_2$, and washed with water, 10% NaHCO$_3$, and brine. The organic layer is then dried over Na$_2$SO$_4$, and purified by silica gel chromatography to deliver 7-O-protected paclitaxel.

a. 7-O-TROC-paclitaxel (21)

Following the general procedure, 7-O-TROC-baccatin III 6 (158.4 mg, 0.21 mmol) in 4.6 mL of THF was reacted with BMOP 24 (137 mg, 0.40 mmol) and LiHMDS (0.25 mL, 0.25 mmol) to produce 139.5 mg 139.5 mg 79% of 7-O-TROC-baccatin III.

b. Paclitaxel from 7-O-TROC-paclitaxel (21)

7-O-TROC-paclitaxel 21 (130 mg, 0.13 mmol) was reacted with Zn dust (150 mg, 2.29 mmol) in AcOH-MeOH (1:1, 5 mL) at 60° C. for 2.5 h. The reaction mixture was cooled and filtered and the organic solvent was evaporated. The resulting residue was purified by colulmn chromatography to yield paclitaxel (88.3 mg) in 81.9% yield.

c. 7-O-CBZ-paclitaxel (22)

Following the general procedure, 7-O-CBZ-baccatin III 10 (156.5 mg, 0.22 mmol) in 2 mL of THF was reacted with BMOP 24 (94.7 mg, 0.28 mmol) and LiHMDS (0.24 mL, 0.24 mmol)) to produce 139.5 mg 61% of 7-O-CBZ-paclitaxel.

d. Paclitaxel from 7-O-CBZ-paclitaxel (22)

7-O-CBZ-paclitaxel 22 (115 mg, 0.12 mmol) was hydrogenated (30 psi H$_2$, 20 mg of 10% Pd/C in 20 mL of absolute ethanol for 3 h. The reaction mixture was washed with 10 mL of CH$_2$Cl$_2$. The combined filtrates were concentrated and chromatographed to give paclitaxel 73.4 mg, 78.1%.

e. Paclitaxel Directly from 7-O-BOC-baccatin III (11) through 7-O-BOC-paclitaxel (23)

Following the general procedure, 7-O-BOC-baccatin III 11 (125 mg, 0.18 mmol;) in 2.5 mL of THF was reacted with BMOP 24 (125 mg, 0.37 mmol) and LiHMDS (0.22 mL 0.22 mmol) to produce crude 7-O-BOC-paclitaxel, which was not isolated, but further reacted with TFA (60 μL, 0.78 mmol) and water (0.316 mL) in AcOH (1.25 mL) for 51 h to produce 57.4 mg (55.2%) of paclitaxel.

I claim:

1. A process for preparing paclitaxel by converting baccatin III into 7-O-acyl-protected baccatin III in good yield and high quality with an electrophilic protecting group of the formula

wherein R is alkyl, aryl, R'O—, or R'$_2$N—, R'S, and X is halogen, imidazoyl, benztriazole, N-(benzyloxycarboxyloxy) succinimide, OR', or —OOCOR, with a strong base in a solvent of the general formula, R—CONR'$_2$, and wherein R' is alkyl or alkenyl having 1–6 carbon atoms, benzyl, phenyl, trichloroethyl, trifluoroethyl, 2-trimethylsilylethyl or triisopropylsilyl.

2. A process according to claim 1, wherein said solvent is selected from the group consisiting of DMF, DMAC, NMPO, DMEU and DMPU.

3. A process according to claim 2, wherein said solvent is DMF.

4. A process according to claim 1, wherein said strong base has the general formula R—O$^-$M$^+$, wherein R is alkyl or aryl, and M is a metal selected from the group consisting of lithium, sodium or potassium.

5. A process according to claim 1, wherein said strong base is selected from the group consisting of LiHMDS, LitbuO, KHMDS or NaHMDS in DMF.

6. A process according to claim 5, wherein said strong base is LitbuO.

7. A process according to claim 1, wherein said electrophilic protecting group is selected from the group consisting of CBZ-Cl, CBZ$_2$O, CBZ-benztriazole, BOC-Cl or BOC$_2$O, TROC-Cl diethylchlorophosphate, isobutyl chloroformate, acetylimidazole, adamantyl fluoroformate, allyl chloroformate, or vinyl chloroformate.

8. A process for synthesizing paclitaxel of the formula:

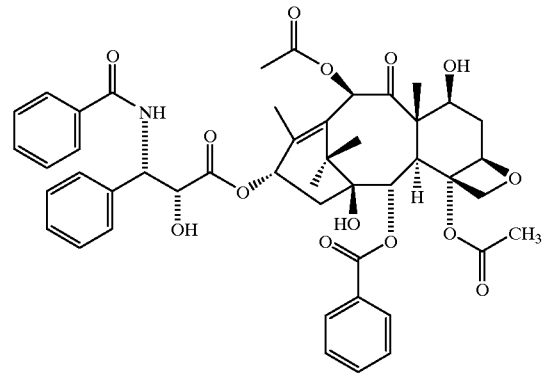

comprising the steps of;

a. treating a solution of baccatin III having the formula

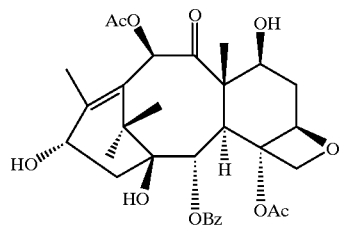

with a strong base in a solvent;

b. Adding an electrophile to the solution to form a 7-O-protected baccatin III derivative having the formula

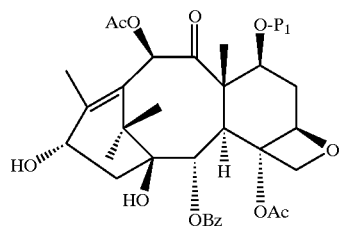

c. Reacting the 7-O-protected baccatin III derivative with a protected paclitaxel sidechain in a solvent, such that said sidechain is coupled with said 7-O-protected baccatin III derivative at the C-13 position, d. Deprotecting said protected paclitaxel sidlechain and removing said 7-O protecting group to form paclitaxel.

9. The process according to claim 8, wherein said solvent is DMF.

10. The process according to claim 8, wherein said strong base is selected from the group consisting of LitbuO, LiHMDS, KHMDS, NaHMDS.

11. The process according to claim 8, wherein said electrophile is selected from the group consisting of CBZ-Cl, $CBZ_2O$, CBZ-benztriazole, BOC-Cl or $BOC_2O$, diethylchlorophosphate, isobutyl chloroformate, acetylimidazole, adamantyl fluoroformate, allyl chloroformate, vinyl chloroformate.

12. The process according to claim 8, wherein said protected paclitaxel sidechain is attached to the C-13 hydroxyl of said 7-O-protected baccatin III derivative using a dehydrating agent.

13. The process according to claim 12, wherein said dehydrating agent is DCC.

14. The process according to claim 12, wherein said dehydrating agent is toluene with DCC and DMAP.

15. The process according to claim 8, wherein said protected paclitaxel sidechain is attached to the C-13 hydroxyl of said 7-O-protected baccatin III derivative using a strong base.

16. The process according to claim 15, wherein said strong base is LitbuO or butyllithium.

17. The process according to claim 8, wherein said step of deprotecting said protected sidechain and removing said 7-O-protecting group from said 7-O-protected baccatin III derivative is performed by acid hydrolysis.

18. The process according to claim 8, wherein said paclitaxel sidechain is a β-phenylisoserine sidechain.

* * * * *